United States Patent [19]
Heitmann et al.

[11] Patent Number: 4,644,176
[45] Date of Patent: Feb. 17, 1987

[54] METHOD AND APPARATUS FOR SCANNING THE EXTERIOR OF ROD-SHAPED ARTICLES OF THE TOBACCO PROCESSING INDUSTRY

[75] Inventors: Uwe Heitmann; Peter Pinck; Berthold Maiwald, all of Hamburg, Fed. Rep. of Germany

[73] Assignee: Hauni-Werke Körber & Co. Kg., Hamburg, Fed. Rep. of Germany

[21] Appl. No.: 616,952

[22] Filed: Jun. 4, 1984

[30] Foreign Application Priority Data

Jun. 3, 1983 [DE] Fed. Rep. of Germany ....... 3320199
Dec. 31, 1983 [DE] Fed. Rep. of Germany ....... 3347702

[51] Int. Cl.$^4$ .............................................. G01N 21/88
[52] U.S. Cl. ..................................... 250/572; 250/239
[58] Field of Search ...................... 356/237, 239, 240; 209/535, 536, 540; 250/233 B, 214 RC, 572

[56] References Cited

U.S. PATENT DOCUMENTS

4,483,615 11/1984 Bieringer et al. .................. 356/237

Primary Examiner—Gene Wan
Attorney, Agent, or Firm—Peter K. Kontler

[57] ABSTRACT

The exterior of successive filter cigarettes, filter rod sections or other rod-shaped articles of the tobacco processing industry is monitored for the presence of various defects including absence or improper orientation of filter mouthpieces, improperly applied or outwardly projecting uniting bands, absence of roundness and/or others by directing a beam of radiation along successive articles while they move sideways in the flutes of a drum-shaped conveyor. The beams of radiation are influenced by defects and are thereupon monitored for the purposes of generating signals which are indicative of defects, if any. The beam of radiation extends all the way along the full length of each article and can also extend partially or around the entire circumference of each article.

27 Claims, 9 Drawing Figures

METHOD AND APPARATUS FOR SCANNING THE EXTERIOR OF ROD-SHAPED ARTICLES OF THE TOBACCO PROCESSING INDUSTRY

BACKGROUND OF THE INVENTION

The present invention relates to a method and apparatus for monitoring cigarettes and/or other rod-shaped articles of the tobacco processing industry, and more particularly to improvements in methods and apparatus for scanning the exterior of such rod-shaped articles. Still more particularly, the invention relates to improvements in a method and apparatus for optically or similarly scanning the exterior of cigarettes or similar rod-shaped articles for the presence or absence of certain types of defects which can be detected by resorting to light or other forms of radiation.

The exterior of cigarettes, filter rod sections and/or analogous rod-shaped articles of the tobacco processing industry is likely to exhibit a number of defects, such as open seams, holes, enlarged portions, improperly applied or improperly oriented filter mouthpieces, absence of filter mouthpieces, bends in the tobacco-containing or filter-containing portions of filter cigarettes, cigars or cigarillos, absence of roundness, frayed or open tobacco-containing end portions of cigarettes, cigars or cigarillos, improperly applied uniting bands of tipping paper which is used to affix filter mouthpieces to plain cigarettes, cigars or cigarillos and/or a combination of two or more of the above-enumerated defects.

It is already known to monitor the exterior of a rod-shaped article of the tobacco processing industry with light or other types of radiation. Changes in the characteristics of radiation which are indicative or suggestive of the presence of one or more defects are detected by resorting to a suitable transducer, and the signals which are furnished by the transducer are used to segregate defective articles from satisfactory articles and/or to effect changes which are intended to prevent persistence and/or future development of similar defects in a cigarette rod making, filter tipping, filter rod making or like machine. For example, U.S. Pat. No. 4,011,950 to McLoughlin et al. discloses a cigarette monitoring apparatus wherein light rays are caused to pass along a portion of the periphery of the tested cigarette, namely along the filter plug or filter mouthpiece of a filter cigarette, in order to ascertain whether or not the filter mouthpiece is properly oriented with reference to the tobacco-containing portion of such product. The patented apparatus is further supposed to detect improperly convoluted and/or outwardly extending portions of uniting bands of tipping paper. A drawback of the patented apparatus is that the light source and/or the photoelectric sensor can only be placed close to but not all the way into contact with the periphery of the tested article. This means that such apparatus cannot detect defects which can be detected only if the radiation is caused to propagate itself in immediate proximity of the exterior of the article. For example, a partially projecting portion of a uniting band will not be detected if it does not extend outwardly well beyond the major part of the tested article. This reduces the versatility and particularly the reliability of such monitoring apparatus.

U.S. Pat. No. 4,277,678 to Wahle et al. discloses a modified method and apparatus for testing cigarettes or the like. The article to be tested is set in motion to rotate about its own axis and to thereby move its periphery along a beam of radiation which is caused to propagate itself in parallelism with the axis of the rotating article. The radiation source emits a single light beam which is caused to pass along the entire article and thereupon impinges upon a photoelectric transducer. This method and the apparatus for its practice are quite reliable; however, they can be put to use only under circumstances when the articles to be tested are or can or should be caused to rotate about their own axes.

OBJECTS AND SUMMARY OF THE INVENTION

An object of the invention is to provide a novel and improved method of monitoring the exterior of cigarettes or analogous rod-shaped articles of the tobacco processing industry in such a way that the entire exterior or nearly the entire exterior of an article can be tested without necessitating rotation of the article about its own axis.

Another object of the invention is to provide a method which can be used with advantage for detection of a wide variety of externally detectable defects in the wrappers and/or fillers of plain or filter tipped cigarettes, cigars or cigarillos as well as in the wrappers and/or fillers of discrete filter rod sections.

A further object of the invention is to provide a method which can be resorted to for simultaneous detection of one, more or all of a wide variety of defects which are likely to develop in or at the exterior of rod-shaped articles of the tobacco processing industry.

An additional object of the invention is to provide a method which can be practiced for detection of defects in or at the exterior of selected portions of or entire rod-shaped articles of the tobacco processing industry.

Still another object of the invention is to provide a novel and improved apparatus for the practice of the above outlined method.

Another object of the invention is to provide an apparatus whose versatility and reliability exceed those of heretofore known apparatus and which can be installed in existing cigarette rod making, filter rod making, filter tipping and analogous machines.

An additional object of the invention is to provide the apparatus with novel and improved means for conducting radiation along the exterior of a rod-shaped article of the tobacco processing industry.

A further object of the invention is to provide novel and improved articles supporting and advancing means for use in the above outlined apparatus.

An additional object of the invention is to provide the apparatus with novel and improved means for generating and evaluating signals which denote the presence and/or absence of one or more defects in or at the exterior of plain or filter tipped cigarettes, filter rod sections and the like.

A further object of the invention is to provide the apparatus with novel and improved means for simultaneously or sequentially monitoring rod-shaped articles for the presence or absence of identical or different defects.

An additional object of the invention is to provide an optical scanning apparatus which can readily discriminate between serious defects (which warrant segregation or discarding of the respective articles) and defects which do not sufficiently affect the appearance, quality and/or other characteristics of the tested articles to warrant their segregation from other articles.

Another object of the invention is to provide the apparatus with novel and improved means for generating signals which allow for classification of various types of defects.

One feature of the invention resides in the provision of a method of testing a cigarette or an analogous rod-shaped article for the presence or absence of defective portions in and close to the exterior of the article. The method comprises the steps of moving the article to be tested along a predetermined path at least substantially at right angles to its axis (it is immaterial whether or not the article rotates about its axis while moving along such path), directing at least one beam of radiation (e.g., visible light) closely adjacent to the exterior, in at least substantial parallelism with the axis and along the full length of the article whereby the characteristics of radiation change under the influence of defective portions (if any) which enter the path of radiation, monitoring the characteristics of radiation which has passed along the article, and generating signals denoting the monitored characteristics of the radiation.

The directing step can comprise directing at least one beam of radiation along an arcuate portion at least of the circumference (or along the entire circumference) of the article in the path. Such portion of the circumference can extend along an arc of at least 90 degrees in order to ensure an examination of at least 25 percent of the exterior of the article.

In accordance with a presently preferred embodiment of the method, the cross-sectional area of the beam of radiation in a plane extending at right angles to the direction of propagation of radiation exceeds the cross-sectional area of the article, as considered at right angles to the axis of the article, at least in the region of the aforementioned portion of the circumference of the article.

The beam of radiation can constitute a solid cylinder having a cross-sectional area which exceeds the cross-sectional area of the moving article, and the directing step then preferably comprises directing the solid cylinder axially against one end face of the article so that the latter intercepts the central portion of the solid cylinder and permits a hollow cylindrical portion of radiation to propagate itself along the exterior of the article. The beam extends transversely of a predetermined portion of the path for the article so that the hollow cylindrical portion of radiation is formed only while the article moves along such predetermined portion of the path.

The method can further comprise the step of splitting the beam of radiation into several smaller streams. The monitoring step then preferably comprises separately monitoring each smaller stream, and the signal generating step then comprises generating discrete signals denoting the monitored characteristics of the respective smaller beams. Such method preferably further comprises the step of establishing and maintaining a single source of radiation for the formation of the original beam and conveying each smaller beam through a discrete confining aperture of a diaphragm prior to the respective monitoring step. The splitting step can comprise passing the beam through a partially transmitting optical element (such as a suitable mirror) before the radiation reaches the article in the path, and such method preferably further comprises the step of reflecting the smaller beams back through the optical element subsequent to propagation along the article and prior to the monitoring step.

The monitoring step can include directing the entire radiation (e.g., the entire hollow cylindrical portion of the originally solid cylindrical beam of radiation) against a single transducer.

Another feature of the invention resides in the provision of an apparatus for testing a cigarette or an analogous rod-shaped article of the tobacco processing industry for the presence or absence of defective portions in or close to the exterior of the article. The apparatus comprises transporting means for moving the article at least substantially at right angles to its axis along a predetermined path, at least one source of radiation, means for directing at least one beam of radiation from the source transversely of the path so that the radiation is propagated in immediate proximity of the exterior, in parallelism with the axis and along the full length of the article in the path whereby the characteristics of radiation change under the influence of defective portions (if any) which enter the path of such radiation, and means for monitoring the characteristics of radiation, including means for generating signals denoting the monitored characteristics.

The directing means can comprise means for effecting the propagation of radiation along a portion at least of the circumference (or nearly along the entire circumference) of the moving article. For example, such propagation effecting means can be designed to effect the propagation of radiation along an arc of at least 90 degrees, as considered in the circumferential direction of the article. The just discussed propagation effecting means can be designed to impart to the beam of radiation a cross-sectional area which, in a plane that is normal to the direction of propagation of the radiation, is greater than the cross-sectional area of the article in a plane that is normal to the axis of the article.

The directing means can comprise means for effecting the propagation of a hollow cylindrical beam of radiation around a portion at least of the article in the path; this can be achieved by imparting to the beam that issues from the source a solid cylindrical shape and by using optical means for directing the beam axially against one end face of the article in the path. If the diameter of the solid cylindrical beam exceeds the diameter of the article, the latter is surrounded by a hollow cylindrical beam of radiation during travel along that portion of the path which is adjacent to the directing means.

The apparatus can further comprise means for splitting the beam into a plurality of smaller beams, and the monitoring means then preferably comprises a discrete transducer for each smaller beam. The beam splitting means can comprise diaphragm means having apertures for the smaller beams. Alternatively, or in addition to the diaphragm means, the beam splitting means can comprise a partially transmitting first mirror which extends across the beam of radiation between the source and the path, and such apparatus preferably further comprises a fully reflecting second mirror which is adjacent to the path of the article opposite the first mirror and serves to reflect influenced radiation back against the first mirror which is arranged to direct the thus reflected radiation against the transducers.

As mentioned above, the directing means can comprise means for converting the radiation which issues from the source into a hollow cylinder (either with or without assistance from the article in the path) not later than on entry of radiation into contact with the article, and the monitoring means can comprise a single transducer for the entire hollow cylindrical beam of radiation.

The transporting means comprises a rotary drum or another suitable conveyor which is preferably provided with at least three supporting portions for an article in the path. Such supporting portions are preferably spaced apart from one another, as considered in the circumferential direction of the article in the path, and the area of contact between each of the supporting portions and the exterior of the article is preferably a small fraction of the area between two neighboring supporting portions. Such supporting portions can include narrow elongated ribs which extend in substantial parallelism with the article in the path. The ribs can include a centrally located rib and two additional ribs which flank the centrally located rib, which are parallel thereto and which are equidistant therefrom. The ribs can be provided in a flute which is formed in the conveyor for the rod-shaped article. The conveyor can be provided with at least one suction port which attracts the article to the supporting portions during transport past the monitoring station. For example, the conveyor can have a plurality of suction ports which are disposed between the supporting portions.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
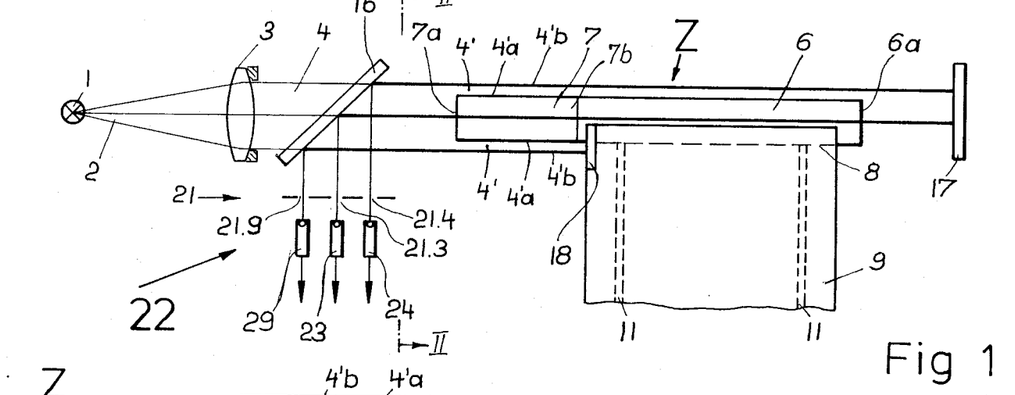
FIG. 1 is a fragmentary schematic elevational view of a monitoring apparatus which embodies one form of the invention and is provided with beam splitting means serving to direct several smaller beams of radiation to discrete transducers.
Figure 2:
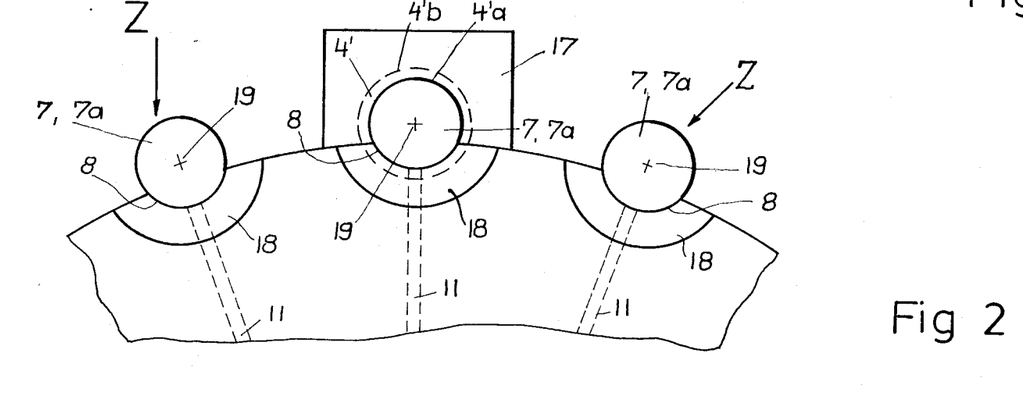
FIG. 2 is a fragmentary end elevational view of the conveyor as seen in the direction of arrows from the line II—II in FIG. 1.

Referring first to FIGS. 1 and 2, there is shown a portion of a monitoring apparatus which serves to scan the exterior of a succession of rod-shaped smokers' articles Z each of which constitutes a filter cigarette having an elongated filter rod section or filter plug 7 and an elongated tobacco-containing portion or plain cigarette 6. The articles Z are transported sideways in the flutes 8 of a drum-shaped conveyor 9 which is formed with radially extending suction ports 11 terminating in the flutes 8 so as to attract the articles Z during travel of such articles from a first station where they are inserted into successive flutes 8 to a second station where they are removed from the corresponding flutes and are introduced into the flutes of a next-following drum-shaped conveyor or onto the upper reach of an endless belt conveyor for delivery to storage or to a packing machine, not shown. The periphery of the conveyor 9 defines an elongated arcuate path for the transport of successive articles Z at right angles to the axes of such articles.

The monitoring apparatus further comprises means for directing radiation issuing from a suitable source 1 (for example, a source of visible light) in parallelism with the axes of successive articles Z. The radiation directing means comprises an optical element in the form of a lens 3 serving to convert radiation 2 issuing from the source 1 into a solid cylindrical beam 4 a portion of which is caused to pass through a partially transmitting mirror 16 that extends at an oblique angle to the axis of the cylinder 4 and is disposed between the source 1 and the adjacent exposed end face 7a of the filter plug 7 forming part of the article Z at the monitoring station. The radiation source 1 is preferably stationary, the same as the optical elements 3 and 16 so that successive articles Z enter into the path of the radiation cylinder 4 only during a relatively short interval of time which elapses during travel of such articles along the corresponding portion of the arcuate path which is defined by the conveyor 9.

The purpose of the solid cylindrical beam 4 of radiation is to ascertain the presence or absence of various defects at or close to the exterior of each article Z which traverses the path of such radiation. For example, the beam of radiation can be influenced by improper draping of the uniting band 7b which is utilized to connect the filter plug 7 with the tobacco-containing portion 6 of the respective article Z. In addition, the radiation of the beam 4 can be influenced by improper orientation of the filter plug 7 relative to the tobacco-containing portion 6 and/or vice versa. Still further, the radiation of the beam 4 can be influenced by the absence of the filter plug 7 or by such application of the uniting band 7b that a portion thereof extends radially or otherwise outwardly beyond the general outline of the respective article Z.

As can be seen in FIG. 1, each article Z is inserted into the respective flute 8 in such a way that the entire uniting band 7b is disposed at one side of the conveyor 9 and that only the tobacco-containing portion 6 is actually received in the respective flute. Such insertion of articles Z is effected by the conveyor or other suitable means (for example, a drum-shaped conveyor) which delivers the articles into the flutes 8 at the aforementioned first station. Reference may be had, for example, to commonly owned U.S. Pat. No. 3,527,234 granted Sept. 8, 1970 to Alfred Hinzmann. This patent discloses suitable means for delivering rod-shaped articles to a rotary drum-shaped conveyor as well as means for receiving such articles from the conveyor at two angularly spaced points of the conveyor. The manner in which the ports 11 of the drum-shaped conveyor 9 are connected with a suction generating device (for example, with the suction intake of a fan) is also known in the art of making and processing cigarettes and other rod-shaped articles of the tobacco processing industry. For example, the ports 11 can be connected to or sealed from the suction intake of a fan by one or more stationary valve plates which are adjacent to the end faces of the conveyor 9 and ensure that the pressure in the ports 11 is below atmospheric pressure at the time when such ports advance from the aforementioned first to the aforementioned second station. This ensures that each article Z which advances past the monitoring station (where the solid cylindrical beam 4 of radiation impinges upon the normally white end faces 7a of filter plugs 7 of successive articles Z) is securely attracted to the conveyor 9 and does not change its position relative to the corresponding flute 8 during impingement of radiation thereagainst. When an article Z reaches the second station, the corresponding ports 11 are sealed from the suction generating device so that such article is readily transferred onto the next conveyor for further processing.

The partially transmitting mirror 16 can be designed in such a way that it intercepts one-half of radiation issuing from the source 1 and passing through the optical element 3 and permits the remaining half of such radiation to constitute a weaker solid cylindrical beam which impinges against the end faces 7a of filter plugs 7 of successive articles Z.

Figure 3:
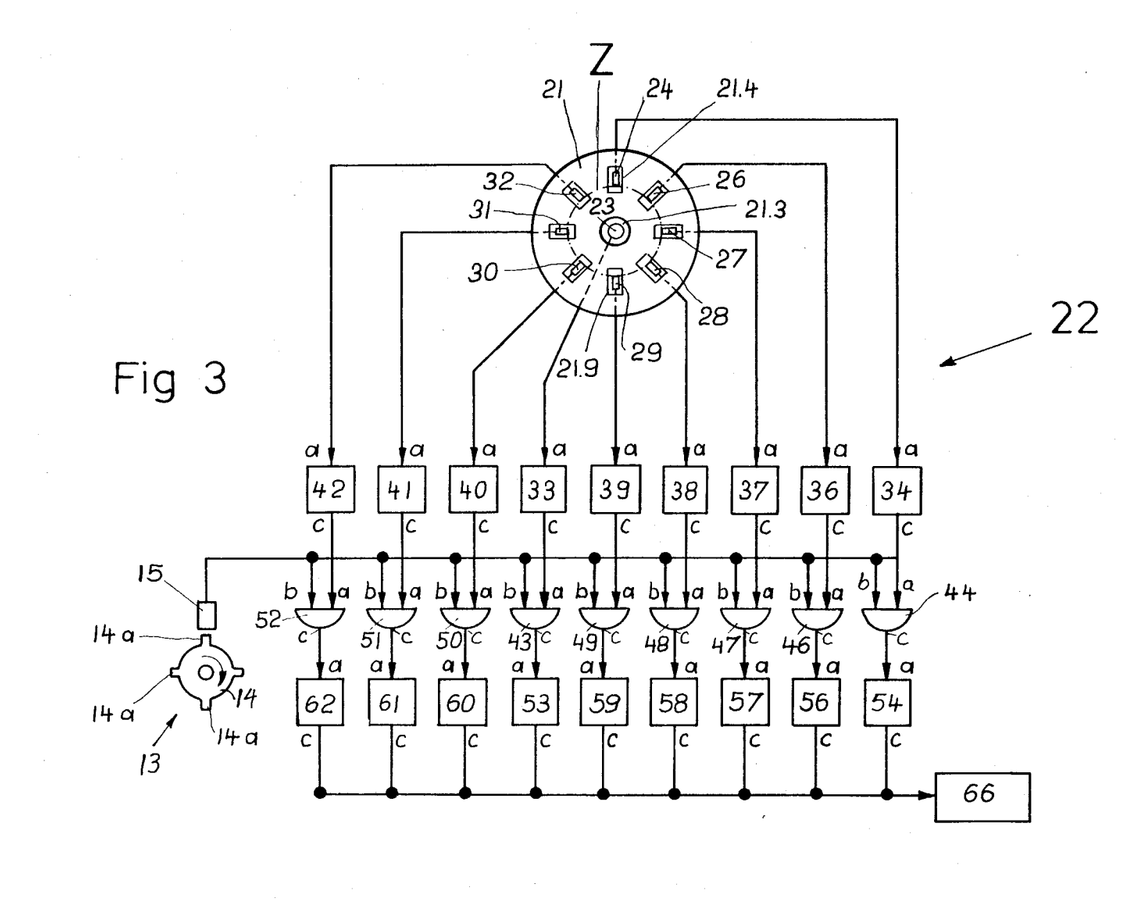
FIG. 3 is a diagrammatic view of an evaluating circuit for signals which are generated in the apparatus of FIGS. 1 and 2.

The optical system of the monitoring apparatus further comprises arcuate mirrors 18 which are mounted on the conveyor 9 adjacent to those ends of the flutes 8 which face toward the mirror 16. The mirrors 18 can totally reflect the impinging radiation and direct such radiation back toward the corresponding side of the mirror 16. An additional totally reflecting mirror 17 is disposed opposite the mirror 16 (with the conveyor 9 disposed between the mirrors 16 and 17). The purpose of the mirror 17 is to totally reflect radiation which has passed along the exterior of the rod shaped article Z while such article was located in the path of propagation of radiation constituting the cylindrical beam 4. In other words, a portion of radiation which is permitted to reach the path of the articles Z is totally reflected by one of the mirrors 18 and the remainder of such radiation is reflected by the totally reflecting mirror 17. The reflected radiation is invariably directed back against the inclined mirror 16 which causes such radiation to pass through the apertures of a stationary diaphragm 21 (shown schematically in FIG. 1) and thereupon against the photosensitive portions of discrete transducers of which only three (namely those numbered 23, 24 and 29) are actually shown in FIG. 1. The transducers 23, 24 and 29 form part of an evaluating circuit 22 the details of which are illustrated in FIG. 3. The diaphragm 21 has a separate aperture for each of the transducers. In FIG. 1, the apertures which permit reflected light to reach the transducers 23, 24 and 29 are respectively denoted by the reference characters 21.3, 21.4 and 21.9.

When the solid cylindrical beam 4 (and more precisely stated that part of such beam which has been permitted to pass through the mirror 16) impinges upon the oncoming filter plug 7, the end face 7a of the filter plug intercepts the central portion or core of the solid cylindrical beam and permits a hollow cylindrical beam 4' to propagate itself along the exterior of the entire uniting band 7b. A portion of the hollow cylindrical beam 4' is further permitted to propagate itself along that portion of the exterior of the tobacco-containing portion 6 which is not confined in the respective flute 8, and such portion of the beam 4' is then reflected by the stationary mirror 17. A portion of the cylindrical beam 4' is further reflected by the corresponding arcuate mirror 18 and is thereupon deflected by the mirror 16 toward the diaphragm 21. The reference characters 4' denote in FIG. 1 the internal surface of the hollow cylindrical beam 4'. Such internal surface is adjacent to the exterior of the convoluted uniting band 7b and to the exterior of the wrapper of the tobacco-containing portion 6 of the respective rod-shaped article Z. The reference character 6a denotes in FIG. 1 the head or free end of the tobacco-containing portion 6 of the illustrated article Z. The mirrors 18 on the conveyor 9 reflect a portion of the hollow cylindrical beam 4', namely the portion which is adjacent to the external surface 4'b of such hollow cylindrical beam in the region radially inwardly of the axis 19 of the article Z which is located in the path of propagation of radiation issuing from the source 1 and passing through the optical elements 3 and 16 toward the optical elements 17 and 18. The exact configuration of the external surface 4'b of the hollow cylindrical beam 4' depends upon the characteristics and dimensions of the optical element 3. On the other hand, the configuration of the internal surface 4'a of the hollow cylindrical beam 4' depends upon the dimensions of the article Z which is located in the path of radiation from the optical element 3 toward the mirror 17.

FIG. 2 shows that the major part of the hollow cylindrical beam 4' is permitted to pass along the entire article Z at the monitoring station in parallelism with the axis 19 of such article and all the way from the end face 7a of the respective filter plug 7 to and beyond the head 6a of the respective tobacco-containing portion 6. A smaller part of the hollow cylindrical beam 4' is permitted to advance to the corresponding mirror 18 to be reflected back against the corresponding side of the partially reflecting mirror 16. It will be noted that the hollow cylindrical beam 4' is capable of surrounding the entire filter plug 7 at the time when such filter plug is located within the confines of the solid cylindrical beam 4 passing through the mirror 16. At such time, the axis 19 of the corresponding article Z coincides with the optical axis of the element 3.

An important advantage of the feature that the hollow cylindrical beam 4' can surround the entire exterior of each filter plug 7 is at such part of the article Z is most likely exhibit one or more defects of the type capable of being detected on evaluation of radiation which has passed along the article Z and was caused to be reflected against the transducers of the evaluating circuit 22. For example, and as mentioned above, radiation which constitutes the hollow cylindrical beam 4' will be influenced by improper orientation of the filter plug 7 relative to the tobacco-containing portion 6. Furthermore, such radiation will be influenced by improperly applied uniting bands 7b, for example, if such uniting bands exhibit pronounced and excessive undulations or end portions which extend radially, tangentially or otherwise beyond the general circumferential outline of the respective article Z. Still further, radiation of the beam 4 can be utilized to detect the presence or absence of filter plugs 7 because, if a filter plug 7 is absent, radiation impinges upon the darker end face of the tobacco-containing portion 6 in lieu of impinging upon the normally white end face 7a of the filter plug 7. Radiation which has been permitted to advance beyond the mirror 18 on the conveyor 9 on its way toward the totally reflecting mirror 17 can be influenced by the presence or absence of defects at the exterior of the tobacco-containing portion 6. For example, such radiation can be influenced by an open seam of the wrapper of the tobacco-containing portion 6, by the unduly enlarged head 6a of such portion 6 and/or by improper orientation of the portion 6 relative to the conveyor 9. The monitoring action is highly accurate and reliable, especially in the region of each filter plug 7 because the latter is completely surrounded by the hollow cylinder 4'. The angular positions of articles Z which are inserted into the flutes 8 of the conveyor 9 are preferably such that the seams of the wrappers of the tobacco-containing portions 6 do not abut against the surface of the conveyor 9 in the respective flutes 8. This allows for detection of eventual defects or inaccuracies in the formation of seams. As is well known from the art of cigarette making machines, seams are formed by coating one marginal portion of a running web of cigarette paper or the like with an adhesive and thereupon folding such marginal portion over the other marginal portion of the web so that the web is converted into a tube or hollow cylinder which surrounds a filler of tobacco. Reference may be had to U.S. Pat. No. 4,009,722 granted Mar. 1, 1977 to Günter Wahle.

In FIGS. 1 and 2, the dimensions of the flutes 8 are exaggerated for the sake of clarity. In actual practice, the flutes 8 can be much shallower so that the area of contact between the conveyor 9 and the exterior of the articles Z can be reduced to a minimum. All that is necessary is to increase the number of suction ports 11 and/or to intensify the suction in such ports so as to insure that the articles Z are reliably held in proper orientation relative to the conveyor 9 even if the area of actual contact between each article Z and the conveyor 9 is minimal. By reducing the dimensions (depth) of the flutes 8, one ensures that by far the major part of the exterior of each tobacco-containing portion 6 is fully exposed to the radiation of the hollow beam 4' so as to further enhance the accuracy of the monitoring operation.

As a rule, it suffices to totally examine the exterior of each filter plug 7 because such portions of filter cigarettes Z are most likely to exhibit one or more defects. The defects in or at the exterior of a tobacco-containing portion 6 normally include open or partially open seams, frayed ends in the region of the heads 6a, unduly enlarged (expanded) heads 6a or a combination of such defects. Utilization of uniting bands 7b is a frequent source of defects in the region of the filter plugs 7. The improved testing apparatus is capable of reliably reacting to the presence or absence of such defects to thus ensure that each defective article Z is invariably segregated from the satisfactory articles and cannot reach the packing machine and the consumer.

Radiation which is reflected by the end face 7a of a filter plug 7 at the monitoring station, by the corresponding mirror 18, and by the mirror 17 is directed against the mirror 16 and passes through the apertures of the diaphragm 21 on its way toward the corresponding transducers of the evaluating circuit 22. Each of the transducers can constitute a photodiode, a phototransistor, a photocell or the like. As shown in FIG. 3, the evaluating circuit 22 comprises a total nine transducers including a centrally located transducer 23 and an annulus of eight additional transducers 24, 26, 27, 28, 29, 30, 31 and 32 around the centrally located transducer 23. The diaphragm 21 has a total of nine apertures, one for each of the transducers. This diaphragm is a disc with a centrally located aperture 21.3 for the transducer 23 which has a circular outline and eight rectangular apertures (including those shown at 21.4 and 21.9) for the remaining eight transducers. The transducer 23 is designed to receive light which is reflected by the end face 7a of the filter plug 7 forming part of the article Z which cooperates with the optical elements of the monitoring apparatus to form the hollow cylindrical beam 4'. The remaining eight transducers evaluate radiation which has been caused to pass along the corresponding arcuate sections of the exterior of the article Z at the monitoring station.

The outputs of the transducers 23 to 32 are respectively connected to the inputs a of nine pulse shapers 33, 34, 36, 37, 38, 39, 40, 41 and 42. Each of these pulse shapers 33 to 42 can constitute an adjustable threshold circuit of the type known as Schmitt-trigger with an adjustable threshold. The outputs c of the threshold circuits 33 to 42 are respectively connected to the inputs a of corresponding AND gates 43, 44, 46, 47, 48, 49, 50, 51 and 52. The arrangement is such that the outputs c of the threshold circuits 33 to 42 transmit signals when the selected thresholds are exceeded. At such time, each of the threshold circuits transmits a voltage signal of preselected intensity to the input a of the corresponding AND gate (43 to 52). The thresholds of the circuits 33 to 42 are exceeded when the intensity of signals which are furnished by the associated transducers 23 to 32 reaches a preselected value such as is selected by the setting of the corresponding threshold circuits. Thus, the signals at the outputs c of the threshold circuits disappear as soon as the intensity of signals which are transmitted by the associated transducers drops below the preselected threshold value. In the evaluating circuit 22 of FIG. 3, a portion of the exterior of a filter cigarette Z which is located at the monitoring station is considered to be satisfactory when the output signal of the corresponding transducer exceeds the selected threshold value of the associated threshold circuit. The signals at the outputs c of the threshold circuits 33 to 42 disappear as soon as the associated transducers 23 to 32 detect defects in the corresponding portions of the exterior of the article Z at the monitoring station.

The inputs b of all AND gates 43 to 52 are connected with the output of a proximity detector 15 which forms part of a pulse generator 13 and is adjacent to the periphery of a disc 14 driven at a speed which is proportional to the speed of the conveyor 9. The radially extending projections 14a of the disc 14 approach the proximity detector 15 at the same frequency at which the conveyor 9 advances successive articles Z past the monitoring station. The pulse generator 13 ensures that the inputs b of the AND gates 43 to 52 receive signals during the relatively short intervals of time when successive articles Z traverse the beam of radiation issuing from the source 1 and passing through the optical elements 3 and 16 toward the optical element 17 and the oncoming optical element 18 on the conveyor 9. The projections 14a of the disc 14 can constitute lobes consisting of ferromagnetic material which induces the proximity detector 15 to generate a signal in response to movement of an oncoming projection 14a to the position which is shown at the twelve o'clock position of the disc 14.

An advantage of the pulse generator 13 is that it ensures proper operation of the monitoring apparatus irrespective of the peripheral speed of the conveyor 9. Thus, the speed of the disc 14 increases or decreases in response to increasing or decreasing speed of the conveyor 9 so that the generation of pulses by the detector 15 invariably corresponds to the rate of travel of articles Z past the monitoring station for the radiation source 1 and the optical elements 3, 16 and 17.

It is clear that the pulse generator 13 can be omitted if the inputs b of the AND gates 43 to 52 can receive appropriate signals from other timing devices, for example, from signal generating elements which are placed next to the flutes 8 of the conveyor 9. Each such signal generating element can constitute a ferromagnetic part which is mounted in or on the conveyor 9 adjacent to each flute 8 and can influence a stationary proximity detector which is disposed to the left of the mirror 18 shown in FIG. 1. It is also possible to use the conveyed articles Z as a means for initiating the generation of signals for transmission to the inputs b of the AND gates 43 to 52. The signal generating components on the conveyor 9 or on the articles Z can be detected by photoelectric means or the like.

The outputs c of the AND gates 43 to 52 are connected to the inputs a of nine signal inverting stages 53, 54, 56, 57, 58, 59, 60, 61 and 62. The outputs c of the inverting stages 53 to 62 are connected to a defect signal transmitting circuit 66. It is preferred to install suitable diode gates between the outputs c of the inverting circuits 53 to 62 and the input of the circuit 66 in order to prevent mutual influencing of signals which are transmitted by discrete inverting stages. The circuit 66 can comprise a shift register or other suitable time-delay means which is designed to transport defect signals in imitation of the transport of corresponding (defective) articles Z along the path defined in part or entirely by the conveyor 9 and extending on to an ejecting device which segregates the defective article from the remaining articles. Such ejecting device can comprise a nozzle which is connected with a source of compressed air or another gas by a conduit containing a solenoid-operated valve which opens in response to a signal from the circuit 66 to ensure that the nozzle expels the defective article from the corresponding flute of the conveyor 9 or from a conveyor that follows the conveyor 9. An ejecting device which can be utilized to respond to defect signals in order to segregate defective rod-shaped articles from satisfactory articles is disclosed, for example, in commonly owned U.S. Pat. No. 4,120,194 granted Oct. 17, 1978 to Joachim Reuland.

The mode of operation of the monitoring apparatus which is shown in FIGS. 1 to 3 is as follows:

As soon as a filter cigarette Z reaches the monitoring station, namely when the axis 19 of such cigarette coincides with the axis of the optical element 3 shown in FIG. 1, the pulse generator 13 transmits signals to the inputs b of the AND gates 43 to 52. At such time, the filter plug 7 of the cigarette Z at the monitoring station converts the solid cylindrical beam 4 into a hollow cylindrical beam 4' which, as explained above, completely surrounds the respective filter plug 7 as well as the major part of the exterior of the associated tobacco-containing portion 6.

If the quality of the filter cigarette Z at the monitoring station is satisfactory, i.e., if such cigarette contains a filter plug 7 (this is detected by the transducer 23), if the filter plug 7 is properly oriented relative to the conveyor 9 and the associated tobacco-containing portion 6, if the uniting band 7b is properly convoluted around the filter plug 7 and the adjacent inner end of the tobacco-containing portion 6, if the head 6a of the tobacco-containing portion is not unduly enlarged, if the tobacco-containing portion 6 is properly oriented relative to the filter plug 7 and the conveyor 9, if the portion 6 does not have an open seam, if a portion of the uniting band 7b does not extend radially or otherwise beyond the general outline of the filter plug 7 and tobacco-containing portion 6 and/or if the cigarette Z at the monitoring station does not exhibit any other defects which can be detected by the illustrated apparatus, all of the transducers 23 to 32 transmit electric signals of sufficient intensity so that the intensities of such signals exceed the thresholds which are selected by the setting of the corresponding threshold circuits 33 to 42. Accordingly, the outputs c of the threshold circuits 33 to 42 transmits signals to the inputs a of the associated AND gates 43 to 52 at the time when the inputs b of such gates receive signals from the detector 15. The signals at the outputs c of the gates 43 to 52 are transmitted to the inputs a of the inverting stages 53 to 62 so that the outputs c of such stages do not transmit any signals to the circuit 66. This will be readily appreciated since an inverting stage does not transmit a signal if its input receives a signal. Consequently, the circuit 66 transmits a signal (for example by not transmitting any signals) which is indicative of an acceptable or satisfactory filter cigarette Z, namely a cigarette which should be permitted to enter the packing machine, the storage or another processing station.

However, if the signal at the output of one of the transducers 23 to 32 is too weak due to the influencing of the corresponding portion of the hollow cylindrical beam 4' by a defect of the article Z at the monitoring station, the corresponding inverting stage does not receive a signal so that the output c of such inverting stage transmits a defect signal to the circuit 66 which transports the signal in the aforedescribed manner and affects segregation of the corresponding filter cigarette Z from satisfactory cigarettes.

It will be readily appreciated that the illustrated apparatus is equally capable of monitoring the exterior of other types of rod-shaped articles of the tobacco processing industry, such as filter rod sections, plain cigarettes, plain cigarillos or plain cigars. If the articles to be tested are plain cigarettes or plain filter rod sections, the number of transducers can be reduced since a plain cigarette or a filter rod section is not likely to exhibit as many different types of defects as a filter cigarette. This will be appreciated by bearing in mind that the filter plugs, their orientation relative to the plain cigarettes, and the means for attaching filter plugs to plain cigarettes are frequent causes of defects.

An important advantage of the improved monitoring apparatus is that it can detect defects in or at different portions of the exterior of the article at the monitoring station. This is due to the provision of beam splitting means 16, 21 as well as to the provision of a substantial number of transducers each of which can generate a signal in response to detection of a defect in or at a different portion of the exterior of the article at the monitoring station. Furthermore, the provision of adjustable threshold circuits 33 to 42 also contributes to versatility and sensitivity of the monitoring apparatus because the threshold of each of these circuits can be set differently, depending on the portion of the exterior of an article at the monitoring station which is being scanned or inspected by the respective transducer. For example, the transducer which detects the presence or absence of a filter plug can be connected with a threshold circuit whose threshold is selected differently from the threshold of a threshold circuit which receives signals from a transducer monitoring the presence or absence of open seams in the tobacco-containing portion 6, the presence or absence of an enlarged head 6a, the presence or absence of an outwardly extending portion of the uniting band 7b and/or the presence or absence of an improperly oriented filter plug 7 and/or tobacco-containing portion 6.

The illustrated evaluating circuit 22 constitutes but one of a variety of evaluating circuits which can be utilized in connection with the testing apparatus whose components are shown in FIGS. 1 and 2. For example, the evaluating circuit 22 can comprise a discrete evaluating unit for each of the transducers 23 to 32. This allows for a more reliable and predictable classification of defects which are detected on successive articles and for more reliable adjustment of the machine which produces the articles Z for the purpose of eliminating more frequently occurring or more serious defects. In many instances, it suffices to connect the outputs of all inverting stages to the input of a common defect signal transmitting circuit 66 which is used to ensure reliable expulsion of each and every article that exhibits one or more defects.

Figures 4, 5, 7:
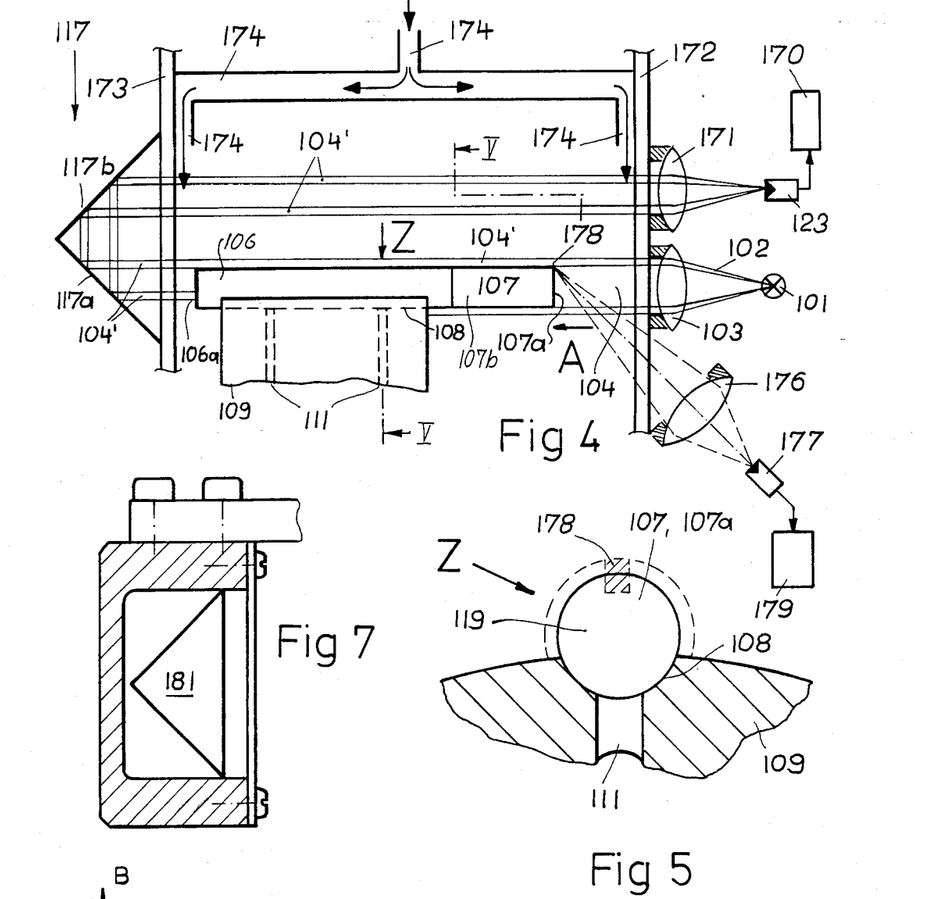
FIG. 4 is a schematic fragmentary elevational view of a second apparatus wherein the monitoring means comprises a single transducer.
FIG. 5 is an enlarged fragmentary transverse sectional view of the conveyor in the second apparatus as seen in the direction of arrows from the line V—V of FIG. 4.
FIG. 7 is a fragmentary sectional view of a modification of the apparatus which is shown in FIGS. 4 and 5.

FIGS. 4 and 5 illustrate a second embodiment of the improved monitoring apparatus. All such parts of this second apparatus which are identical with or clearly analogous to the corresponding parts of the first apparatus are denoted by similar reference characters plus 100. One of the differences between the two apparatus is that, in FIGS. 4 and 5, all of the radiation which issues from the source 101 and is caused to travel along the exterior of a rod-shaped article Z is directed against a single transducer 123. Radiation 102 which issues from the source 101 passes through an optical element 103 which converts it into a solid cylindrical beam 104. The hollow cylindrical portion 104' of the beam 104 impinges upon one internal surface 117a of a substantially L-shaped fully reflecting mirror 117 and is reflected against a second reflecting surface 117b which, in turn, directs such radiation against the transducer 123 by way of an optical element 171. The major part of the hollow cylindrical radiation beam 104' advances along the entire article Z which is then located at the monitoring station. The only exception is that portion of the exterior of the article which is in contact with the flute 108 in the rotary drum-shaped conveyor 109. Such conveyor is again formed with suction ports 111 which attract that part of the exterior of the tobacco-containing portion 106 of the article Z which contacts the respective flute 108. The path of the reflected radiation beam 104' between the surface 117b and the optical element 171 is parallel to the axis 119 of the article Z at the monitoring station. The optical element 171 is a lens which focuses the radiation 104' upon the transducer 123. The latter is connected with an evaluating circuit 170. The manner in which the circuit 170 evaluates radiation that has been influenced by the defects (if any) of the article Z at the monitoring station forms no part of the invention. Such evaluating circuit can be constructed in a manner similar to that of the circuit 22 shown in FIG. 3, i.e., the transducer 123 can transmit signals to a threshold circuit which transmits signals to an inverting stage by way of a suitable logic circuit, such as an AND gate, and the output of the inverting stage transmits signals to a defect signal transporting circuit serving to propagate such signals to an ejecting device. In accordance with a modification, the signal which is transmitted by the transducer 123 is simply compared with a reference signal in a signal comparing stage, and the output of the comparing stage transmits a defect signal whenever the intensity or another characteristic of the signal at the output of the transducer 123 deviates from a range of acceptable values. The timing of transmission of signals from the transducer 123 to the evaluating circuit 170 can be selected by resorting to a pulse generator analogous to the unit 13 shows in FIG. 3.

The drum-shaped conveyor 109 of the apparatus shown in FIGS. 4 AND 5 is disposed between two stationary glass walls 172 and 173 which separate it from the actual optical system of the modified monitoring apparatus. In other words, the mirror 117 is outwardly adjacent to the glass wall 173 and the optical elements 103, 171 are outwardly adjacent to the glass wall 172. This reduces the likelihood of contamination of optical elements 117, 103 and 171 by dust and/or other impurities which may be floating in the atmosphere in the region of the conveyor 109. In order to further reduce the likelihood of contamination of optical elements and distortion of signals which are transmitted to the transducer 123, dust and other solid particulate matter can be held away from the inner sides of the glass walls 172, 173 by currents of clean air which are circulated by a system of conduits 174.

In the embodiment which is shown in FIGS. 4 and 5, the reflected hollow radiation beam 104' is guided from the surface 117b of the mirror 117 toward the optical element 171 along a path which is radially outwardly adjacent to the article Z at the monitoring station. However, it is equally possible to construct or configurate the mirror 117 in such a way that the path of the reflected beam 104' is laterally adjacent to the monitoring station. Furthermore, it is not absolutely necessary that the reflected radiation be parallel to the article Z at the monitoring station.

The apparatus of FIGS. 4 and 5 further comprises an auxiliary monitoring unit which serves to direct a portion of radiation issuing from the source 101 and passing through the optical element 103 against a second transducer 177 connected to an evaluating circuit 179. Radiation which is directed against the transducer 177 is reflected by a portion of the end face 107a of the filter plug 107 of the article Z at the monitoring station and passes through an optical element 176 which focuses such radiation upon the transducer 177. A marker 178 which reflects radiation differently from the remainder of the end face 107a is imaged in a manner as shown in FIG. 5. The position of the marker 178 is such that approximately one-half of it normally overlies the adjacent marginal portion of the end face 107a and the other half extends radially outwardly therefrom. If the filter plug 107 is not in exact axial alignment with the tobacco-containing portion 106 of the article Z at the monitoring station, for example, if the filter plug is slightly inclined with reference to the portion 106, the marker 178 is located entirely within the confines of the end face 107a or is located outside of such end face. Such deviations of the position of the marker 178 relative to the end face 107a are detected by an evaluating circuit 179 in response to corresponding signals from the transducer 177. The signal which is transmitted by the transducer 177 can further indicate the direction of undesirable inclination of the filter plug 107 relative to the tobacco-containing portion 106. Thus, if the entire marker 178 is located within the confines of the end face 107a, the filter plug 107 is inclined in one direction. On the other hand, if the entire marker 178 is located outside of the confines of the end face 107a, the inclination of the filter plug 107 relative to the tobacco-containing portion 106 is in a different direction. Such deviations are interpreted by the evaluating circuit 179 as defects which should result in segregation of corresponding articles Z from satisfactory articles.

The mode of operation of the monitoring apparatus of FIGS. 4 and 5 are as follows:

The beam 102 of radiation which issues from the source 101 passes through the optical element 103 and is converted into a solid cylindrical beam 104. When the solid beam 104 impinges upon the end face 107a of the article Z at the monitoring station, it is converted into a hollow cylinder 104' which is caused to propagate itself along the major part of the exterior of the filter plug 107 and the associated tobacco-containing portion 106. The conversion of solid cylindrical beam 104 into a hollow cylindrical beam 104' takes place at the exact instant when the axis 119 of the article Z at the monitoring station coincides with the axis of the optical element 103.

The surface 117a reflects the major part of the hollow cylindrical radiation beam 104' against the surface 117b of the mirror 117. The only part which is not reflected is that which is intercepted by the right-hand end face of the conveyor 109 in the region of the flute 108 for the article Z at the monitoring station. However, the major part of the beam 104' does reach the surface 117a and is reflected by the surface 117b toward the optical element 171 which focuses the reflected radiation upon the transducer 123. Defects which are detectable by the radiation beam 104' include enlargements of the head 106a of the tobacco-containing portion 106, open seams of the portion 106, the absence of filter plugs 107, improper application of the uniting bands 107b or a combination of such defects.

The absence or improper orientation of a filter plug 107 at the monitoring station is detected by the marker 178 in conjunction with the optical element 176 and transducer 177 whereby the latter transmits a corresponding signal to the evaluating circuit 179. This evaluating circuit responds when the intensity of the signal which is transmitted by the transducer 177 is excessive (namely when the marker 178 is completely out of register with the end face 107a of the filter plug 107 at the monitoring station) or when the intensity of such signal is insufficient because the entire marker 178 is located within the confines of the end face 107a of the filter plug 107 at the monitoring station. Signals from the evaluating circuits 170 and 179 can be transmitted to a common ejecting device.

Figure 6:
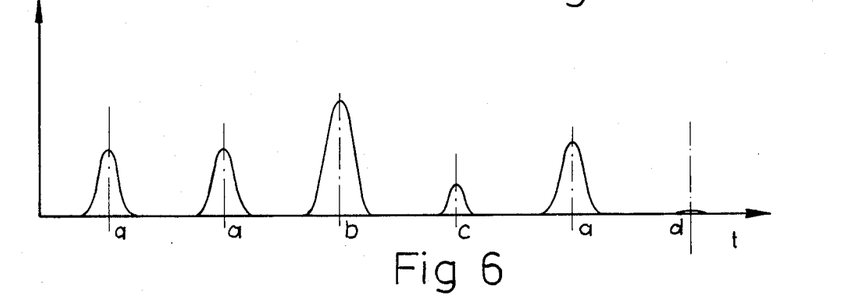
FIG. 6 is a diagram showing various types of signals which can be generated in the improved apparatus.

The diagram of FIG. 6 illustrates a variety of output signals B which are transmitted by the transducer 123 of the monitoring apparatus shown in FIGS. 4 and 5 as a function of time (t). At the instant b, the amplitude of the signal B is very pronounced. This indicates that the filter plug 107 of the article Z at the monitoring station is flexed or bent upwardly and the filter plug is out of register with the corresponding tobacco-containing portion 106. At the instant c, the intensity of the signal B is very low which is indicative of the fact that the inclination of the filter plug 107 relative to the corresponding tobacco-containing portion 106 is in the opposite direction. At the instants a, the orientation of the filter plugs 107 relative to the associated tobacco-containing portions 106 is proper. At the instant d, the intensity of signal B is practically zero; this is indicative of the absence of a filter plug 107.

FIG. 7 illustrates a portion of a monitoring apparatus which constitutes a slight modification of the apparatus shown in FIGS. 4 and 5. The only difference is that the hollow mirror 117 with reflecting surfaces 117a and 117b shown in FIG. 4 is replaced with a radiation reflecting prism 181. In all other respects, the apparatus which embodies the structure of FIG. 7 can be identical with the apparatus of FIGS. 4 and 5.

Figures 8, 9:
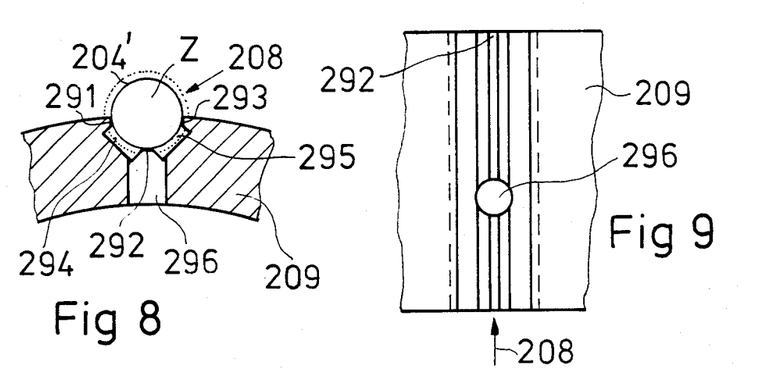
FIG. 8 is a fragmentary transverse sectional view of a modified conveyor which can be used in the apparatus of the present invention.
FIG. 9 is a fragmentary plan view of the conveyor which is shown in FIG. 8.

FIGS. 8 and 9 illustrate a portion of a modified conveyor 209 which can be utilized with advantage in the monitoring apparatus of the present invention. These Figures show only a single flute 208 for a rod-shaped article Z extending in parallelism with the axis of the hollow drum-shaped conveyor 209. The flute 208 contains three spaced-apart elongated rib-shaped supporting portions 291, 292, 293 for the article Z. The arrangement is such that the areas of contact between the supporting portions 291-293 on the one hand and the exterior of the article Z in the flute 208 on the other hand is minimal. In each instance, the area of contact between any one of the supporting portions 291, 292, 293 and the exterior of the article Z is a small fraction of the area of the channel 294 or 295 between two neighboring supporting portions. These channels obviate the need for mirrors (such as 18) at the axial ends of the flutes 208. It will be noted that the centrally located supporting portion 292 is parallel with the supporting portions 291, 293 which flank the portion 292 and are equidistant therefrom.

The reference character 296 indicates one of preferably several suction ports which are provided in the conveyor 209 to attract the article Z to the adjacent surfaces of the supporting portions 291, 292 and 293. It is preferred to provide one or more such suction ports between each pair of neighboring supporting portions in order to ensure reliable retention of the article Z in its flute 208. FIGS. 8 and 9 further show that the overall area of contact between the article Z and the three supporting portions 291, 292, 293 is but a minute fraction of the area of contact between the surface bounding a conventional flute and a rod-shaped article therein.

The channels 294 and 295 permit radiation (such as the hollow cylindrical beam 104' of FIG. 4) to pass therethrough. It will be seen that the narrow elongated supporting portions 291, 292, 293 intercept only a minute fraction of radiation which is intercepted by flutes of the type shown in FIGS. 2 and 5. Consequently, the accuracy of monitoring apparatus which embodies the conveyor of FIGS. 8 and 9 is even more pronounced than that of the previously described apparatus. The outline of the hollow radiation beam 204' is indicated in FIG. 8 by dots. It will be seen that the percentage of radiation forming such hollow beam 204' which is intercepted by the supporting portions 291, 292, 293 is minimal. If desired, the supporting portions 291-293 can be monitored so as to further reduce the percentage of radiation which is held out of contact with the exterior of the article Z in the flute 208.

The manner in which suction in the ports 296 is regulated so as to ensure that the article Z is attracted to the conveyor 209 during travel from the first to the second station is conventional and is not specifically shown in the drawing. As mentioned above, the means for regulating the establishment or termination of a connection between the suction ports and a suction generating device (such as a fan) can include one or more stationary valve plates which are mounted in or adjacent to the conveyor 209.

It will be readily appreciated that the improved apparatus is susceptible of many additional modifications without departing from the spirit of the invention. In its elementary form, the improved apparatus can comprise a single radiation source which transmits a narrow beam of radiation in parallelism with the axis of and along the full length of the rod-shaped article at the monitoring station. However, the provision of means for directing radiation in such a way that the radiation is propagated along a substantial part of the circumference of the article at the testing station is preferred because the results of the monitoring operation are more reliable and more accurate. For example, it would also be possible to direct the radiation in such a way it would extend only along an arc of approximately 90 degrees as considered in the circumferential direction of the article at the monitoring station. In contrast to such simplified apparatus, the apparatus which are shown in the drawing are designed to direct radiation around the entire circumference of the article Z, at least all the way around that portion of the exterior of the article which surrounds the filter plug and the adjacent end portion of the tobacco containing portion of the article if the latter constitutes a filter cigarette, cigar or cigarillo. Radiation which is utilized in the improved apparatus can constitute light rays in the visible or invisible range of the spectrum. However it is also possible to resort to electromagnetic radiation whose frequency is outside of the range that is normally designated as light.

An important advantage of the improved apparatus is that the radiation is caused to pass along the full length of the article at the monitoring station without it being necessary to rotate such article about its own axis in the course of the monitoring operation. Another important advantage of the improved apparatus is that it can monitor the entire exterior of the article at the monitoring station, at least in that region which is more likely to exhibit one or more defects. The exterior of the article which is being tested or which can be tested in the apparatus of the present invention can constitute the external surface of a wrapper made of cigarette paper, imitation cork or a similar wrapping material. Alternatively, the exterior can be a composite exterior which is defined in part by the external surface of a cigarette paper wrapper and in part by a wrapper consisting of tipping paper if the article is a filter cigarette, cigar or cigarillo. If the article is a filter rod section, the exterior is constituted by the external surface of its tubular wrapper which is or can be white. Still further, the exterior can constitute the external surface of a filter rod section which does not necessarily have a discrete tubular envelope but was treated in such a way that the external portion of the filter material constitutes a substantially impermeable layer replacing conventional wrapping material.

The sensitivity of the improved apparatus can be varied practically at will. This depends on the configuration of the beam which issues from the source and is caused to advance toward the article at the monitoring station. The utilization of radiation beams in the form of hollow cylinders is preferred at this time because it ensures detection of the largest number of defects. As can be seen in FIGS. 2 and 5, the cross-sectional area of a solid radiation beam which is directed toward an article at the monitoring station can greatly exceed the cross-sectional area of the article at such station, at least in the region where the hollow portion of such beam surrounds the entire exterior of the article.

The provision of a diaphragm, such as the diaphragm 21 of FIGS. 1 and 3, is desirable and advantageous because splitting of the reflected beam into several smaller or partial beams and the passage of such smaller beams through discrete apertures of the diaphragm reduces the likelihood of undesirable influencing of radiation that is supposed to impinge upon a selected transducer by radiation or radiations that are supposed to impinge upon the neighboring transducer or transducers.

The provision of pulse generator 13 or a similar pulse generating unit is desirable and advantageous when the improved apparatus is used in a modern high-speed cigarette making or analogous machine wherein the interval of time which is allotted for the testing of a single article is extremely short. The pulse generator ensures that the transmission of signals to the evaluating circuit is accurately synchronized with the arrival of an article at the monitoring station. The placing of optical elements of the improved apparatus close or very close to the path of movement of articles through the monitoring station is desirable in order to reduce the likelihood of contamination of such optical elements by dust and other impurities in the surrounding atmosphere. Moreover, such placing of the optical elements close to the path of movement of the articles Z reduces the likelihood that the results of the monitoring operation would be adversely influenced by vibrations or other stray movements of the conveyor or of articles on the conveyor.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A method of testing a cigarette or an analogous rod-shaped article of the tobacco processing industry for the presence of defective portions at the exterior thereof, comprising the steps of moving the article to be tested along a predetermined path at least substantially at right angles to its axis; directing at least one beam of radiation closely adjacent to the exterior, in at least substantial parallelism with the axis and along the full length of the article whereby the characteristics of such radiation change under the influence of defective portions, if any, which enter the radiation; monitoring the characteristics of the radiation; and generating signals denoting the monitored characteristics of the radiation.

2. The method of claim 1, wherein said directing step comprises directing at least one beam of radiation along an arcuate portion at least of the circumference of the article.

3. The method of claim 2, wherein said portion of the circumference extends along an arc of at least 90 degrees.

4. The method of claim 3, wherein the cross-sectional area of the beam in a plane extending at right angles to the direction of propagation of radiation exceeds the cross-sectional area of the article, as considered at right angles to the axis of the article, at least in the region of said portion of the circumference of the article.

5. The method of claim 1, wherein the beam is a solid cylinder having a cross-sectional area exceeding the cross-sectional area of the moving article and said directing step comprises directing the solid cylinder of radiation against one end face of the article so that the latter intercepts the central portion of the solid cylinder and permits a hollow cylindrical portion of radiation to propagate itself along the exterior of the article.

6. The method of claim 5, wherein the beam of radiation extends transversely of a predetermined portion of the path for the article so that said hollow cylindrical portion of radiation is formed only while the article moves along said portion of the path.

7. The method of claim 1, further comprising the step of splitting the beam of radiation into a plurality of smaller beams, said monitoring step including separately monitoring the characteristics of each smaller beam and said signal generating step including generating discrete signals denoting the monitored characteristics of the respective smaller beams.

8. The method of claim 7, further comprising the step of establishing and maintaining a single source of radiation for the formation of the beam and conveying each smaller beam through a discrete confining aperture prior to the respective monitoring step.

9. The method of claim 7, wherein said splitting step comprises passing the beam through a partially transmitting optical element before the radiation reaches the article in said path and further comprising the step of reflecting the smaller beams back through the optical element prior to said monitoring step.

10. The method of claim 1, wherein said monitoring step includes directing the entire radiation against a single transducer.

11. Apparatus for testing a cigarette or an analogous rod-shaped article of the tobacco processing industry for the presence of defective portions at the exterior thereof, comprising transporting means for moving the article at least substantially at right angles to its axis along a predetermined path; at least one source of radiation; means for directing at least one beam of radiation transversely of said path so that the radiation is propagated in immediate proximity of the exterior, in parallelism with the axis and along the full length of the article whereby the characteristics of radiation change under the influence of defective portions, if any, which enter such radiation; and means for monitoring the characteristics of the radiation, including means for generating signals denoting the monitored characteristics.

12. The apparatus of claim 11, wherein said directing means comprises means for effecting the propagation of radiation along a portion at least of the circumference of the moving article.

13. The apparatus of claim 12, wherein said means for effecting the propagation of radiation is arranged to effect such propagation along an arc of at least 90 degrees, as considered in the circumferential direction of the article.

14. The apparatus of claim 13, wherein said means for effecting propagation of radiation comprises means for imparting to the beam a cross-sectional area which, in a plane that is normal to the direction of propagation of radiation, is greater than the cross-sectional area of the article in a plane normal to the axis of the article.

15. The apparatus of claim 11, wherein said directing means comprises means for effecting the propagation of a hollow cylindrical beam of radiation around a portion at least one of the article in said path.

16. The apparatus of claim 11, further comprising means for splitting the beam into a plurality of smaller beams, said monitoring means including a discrete transducer for each smaller beam.

17. The apparatus of claim 16, wherein said splitting means comprises diaphragm means having apertures for the smaller beams.

18. The apparatus of claim 16, wherein said splitting means comprises a partially transmitting first mirror extending across the beam of radiation between said source and said path, and further comprising a fully reflecting second mirror adjacent to said path opposite said first mirror to reflect influenced radiation back against said first mirror, said first mirror being arranged to direct reflected radiation against said transducers.

19. The apparatus of claim 11, wherein said directing means comprises means for converting the beam into a hollow cylinder not later than on entry of radiation into said path, said monitoring means including a single transducer for the entire hollow cylinder of radiation.

20. The apparatus of claim 11, wherein said transporting means comprises a conveyor including at least three supporting portions for the article which is being conveyed along said path.

21. The apparatus of claim 20, wherein said conveyor includes a rotary drum.

22. The apparatus of claim 20, wherein said supporting portions are spaced apart from one another, as considered in the circumferential direction of the article in said path, and the area of contact between each of said supporting portions and the exterior of the article is a small fraction of the area between neighboring supporting portions.

23. The apparatus of claim 20, wherein said supporting portions include narrow elongated ribs extending in substantial parallelism with the article in said path.

24. The apparatus of claim 23, wherein said ribs include a centrally located rib and two additional ribs parallel with and flanking said centrally located rib and being equidistant from the latter.

25. The apparatus of claim 20, wherein said conveyor has a flute for the article and said supporting portions are disposed in said flute.

26. The apparatus of claim 20, wherein said conveyor has at least one suction port which attracts the article to said supporting portions.

27. The apparatus of claim 26, wherein said conveyor has a plurality of suction ports disposed between said supporting portions.

* * * * *